US012636115B2

(12) United States Patent
Gupta et al.

(10) Patent No.: US 12,636,115 B2
(45) Date of Patent: May 26, 2026

(54) OPERATING ROOM LIGHTING SYSTEM

(71) Applicant: Correcting Innovation, LLC, St. Louis, MO (US)

(72) Inventors: Munish Gupta, St. Louis, MO (US); Ellice Gao, St. Louis, MO (US); Bryn Gerwin, St. Louis, MO (US); Justin Guilak, St. Louis, MO (US); Rosemary Lach, St. Louis, MO (US); Renly Liu, St. Louis, MO (US); Hemish Thakkar, St. Louis, MO (US)

(73) Assignee: Correcting Innovation, LLC, St. Louis, MO (US)

( * ) Notice: Subject to any disclaimer, the term of this patent is extended or adjusted under 35 U.S.C. 154(b) by 27 days.

(21) Appl. No.: 18/635,914

(22) Filed: Apr. 15, 2024

(65) Prior Publication Data

US 2024/0407882 A1     Dec. 12, 2024

Related U.S. Application Data

(60) Provisional application No. 63/458,961, filed on Apr. 13, 2023.

(51) Int. Cl.
| | |
|---|---|
| *A61B 90/35* | (2016.01) |
| *A61B 34/00* | (2016.01) |
| *A61B 90/00* | (2016.01) |
| *F21V 21/30* | (2006.01) |
| *G16H 40/63* | (2018.01) |

(52) U.S. Cl.
CPC .............. *A61B 90/35* (2016.02); *A61B 34/25* (2016.02); *A61B 90/361* (2016.02); *F21V 21/30* (2013.01); *G16H 40/63* (2018.01); *A61B 2090/373* (2016.02)

(58) Field of Classification Search
CPC ....... A61B 90/35; A61B 90/361; A61B 34/25; G16H 40/63; F21V 21/30; F21V 21/36
USPC .................................................. 362/269, 257
See application file for complete search history.

(56) References Cited

U.S. PATENT DOCUMENTS

| | | | |
|---|---|---|---|
| 10,925,140 B2 | 2/2021 | Hallack et al. | |
| 11,054,113 B2 | 7/2021 | Hallack et al. | |
| 2008/0192483 A1 | 8/2008 | Mangiardi | |
| 2016/0166333 A1* | 6/2016 | Wang ..................... | A61B 34/10 |
| | | | 600/476 |
| 2018/0036094 A1* | 2/2018 | Aflatoon ............ | H05B 47/1965 |

(Continued)

OTHER PUBLICATIONS

Infrastructure Products: Operating Lights, StarkStrom website (https://starkstrom.com), 2023, 10 pages.

(Continued)

*Primary Examiner* — Edwyn Labaze
(74) *Attorney, Agent, or Firm* — Fleit Intellectual Property Law; Paul D. Bianco

(57)          ABSTRACT

An automated lighting system for operating rooms that aims and focuses light into a work area while eliminating shadows. Mounted to a boom system, akin to traditional operating room lights, or a specially made frame, adjustments to the lighting can be made conveniently, with little or no manual adjustment of the lights. The disclosed automated lighting system allows a surgeon to easily define a target region with some type of user interface, then lights automatically adjust based on the surgeon defined target region to illuminate the target region.

17 Claims, 9 Drawing Sheets

(56)       References Cited

U.S. PATENT DOCUMENTS

2021/0196382 A1\*   7/2021   Mumaw  ................. A61B 90/37
2021/0225506 A1\*   7/2021   Mitchell  ................ G16H 40/63

OTHER PUBLICATIONS

KLS Martin Group, brochure for marLED X Operating lights—
Xtremely Different, Rev. 2020-02, 20 pages.

\* cited by examiner

OPERATING ROOM LIGHTING SYSTEM

FIELD OF THE INVENTION

The invention relates to an operating room lighting system.

BACKGROUND

Many surgical procedures are lengthy, lasting many hours or even more than one day. For example, spinal surgical procedures typically require many hours of surgery with a team of surgical assistants, scrub techs, circulators, anesthesiologists, and spinal cord monitoring technicians. These procedures can be quite taxing physically not only on the patient but also on the members of the surgical team. A surgeon concentrates for long hours on the operating table, placing their body and their neck in positions that over time gets fatigued and painful.

Being in one position bent over the patient's wound or surgical site is one reason for the fatigue and pain in the neck, back, legs, and the shoulders. A survey of members of the Scoliosis Research Society found that neck pain was prevalent in 59% of the respondents.

Overhead surgical lighting directed at the patient's cavity illuminates the surgical site. Current surgical lights are mounted on manual overhead booms, which can be difficult to adjust precisely. Surgeons spend an estimated 25% of the time in the operating room moving the lights to their desired position, attempting to minimize dark spots and reduce shadows. This prolongs the duration of surgery. The overhead light design has been stagnant for decades. Other than changing from incandescent lights to LEDs, most operating rooms utilize the same multiple round set of lights designed decades ago.

In order to adequately visualize deep part of the wounds, a headlight can be worn by the surgeon. Although illumination can be improved by wearing a headlight, there are many issues with headlights. One problem is that the headlights frequently collide with the other surgeons who are also trying to investigate the wound. Every time the surgeons hit their head or the headlights, dust or particles from the head or the headlight can fall into the wound, increasing the risk of wound infection.

In addition, wearing the headlight and trying to properly position the headlight creates extra stress on the neck muscles that are holding the head in that position. Over the hours and hours of being bent over the wound, the neck muscles start to fatigue and become painful giving rise to the neck pain. A typical headlight and the harness around the waist are heavy. The headlight batteries usually need to be replaced in the middle of the procedure. This is not only difficult, since the batteries and harness are located underneath the sterile scrub gown, but also adds extra time to the surgery.

There therefore exists a need for an improved operating room lighting system.

SUMMARY OF THE INVENTION

An operating room lighting system for illuminating a target region of a patient comprises: a plurality of light panels for providing light; a user interface that includes a screen displaying a live stream or recorded video camera image of the patient and an input device usable by a user to select a zone of illumination; a processor for using the live stream or recorded video camera image of the patient and the user selected zone of illumination to calculate yaw, pitch, and focus adjustments of the plurality of light panels to illuminate the target region; and actuator means for using the calculated yaw, pitch, and focus adjustments to move the plurality of light panels so that the provided light from the plurality of light panels illuminates the target region.

In some embodiments, the user interface is a touchscreen monitor that includes the screen displaying the live stream or recorded video camera image of the patient and the input device usable by a user to select a zone of illumination to illuminate the target region.

The plurality of light panels and the processor can be mounted on a mounting structure. This mounting structure can be mounted to an operating room boom. In other embodiments, the mounting structure is mounted to a frame which is made to fit around an operating table holding the patient and to hold the mounting structure at a height so that the plurality of light panels provides light to at least the target region. A video camera can be attached to the frame to provide the live stream or recorded video camera image of the patient.

In an embodiment, each of the plurality of light panels includes a plurality of peripheral lights surrounding a central light. In an exemplary embodiment, each of the plurality of light panels includes six peripheral lights arranged in a hexagonal pattern around a central light. The central light can be a diffuse spotlight or a narrow-angle spotlight and each of the peripheral lights can be a narrow-angle spotlight.

Preferably, the actuator means comprises a separate yaw adjustment assembly, pitch adjustment assembly, and focus adjustment assembly for each of the plurality of light panels.

An embodiment of the separate yaw adjustment assembly for each of the plurality of light panels comprises: a base; a bearing plate from which the plurality of peripheral lights surrounding the central light extend, with the bearing plate rotatably mounted on the base for rotational movement of the bearing plate relative to the base in a plane parallel to a plane of the base, wherein the bearing plate includes a gear cutout; a yaw gear engageable with the gear cutout; and a yaw motor for rotating the yaw gear when actuated.

An embodiment of the separate pitch adjustment assembly for each of the plurality of light panels comprises: a pitch motor; a shaft coupled to the pitch motor to rotate when the pitch motor is actuated; a base member mounted to the bearing plate via brackets and operatively associated with the shaft to rotate when the shaft rotates. One or more arms extend from base member to a pedestal mounted on a platform which holds electrical sockets for the plurality of peripheral lights and the central light.

An embodiment of the separate focus adjustment assembly for each of the plurality of light panels comprises: a focus motor with a lead screw and nut to translate rotational motion into linear motion; a plate holding nut in place; and mechanical linkages extending from the plate to the electrical socket of each of the plurality of peripheral lights. The mechanical linkages include at least one joint and the electrical sockets of the plurality of peripheral lights are pivotably connected to the pivot. Actuation of the focus motor in a first direction causes the plurality of peripheral lights to angle toward the central light and actuation of the focus motor in a second direction causes the plurality of peripheral lights to angle away from the central light.

In an exemplary embodiment, actuation of the yaw motor, pitch motor, and focus motor is controlled by motor control hardware. The motor control hardware can comprise: a microcontroller that receives the calculated yaw, pitch, and focus adjustments and converts the adjustments to yaw, pitch, and focus driver data; a yaw motor driver for receiving the yaw driver data to actuate the yaw motor; a pitch motor driver for receiving the pitch driver data to actuate the pitch motor; and a focus motor driver for receiving the focus driver data to actuate the focus motor.

After the yaw, pitch, and focus adjustments of the plurality of light panels is calculated, the processor can receive user input from the input device to change at least one of the calculated yaw, pitch, and focus adjustments of the plurality of light panels to illuminate the target region.

In an embodiment, each of the plurality of light panels include at least one light that is dimmable.

BRIEF DESCRIPTION OF THE DRAWINGS

A more complete understanding of the present invention, and the attendant advantages and features thereof, will be more readily understood by reference to the following description when considered in conjunction with the accompanying drawings wherein.

DETAILED DESCRIPTION

Figure 1:
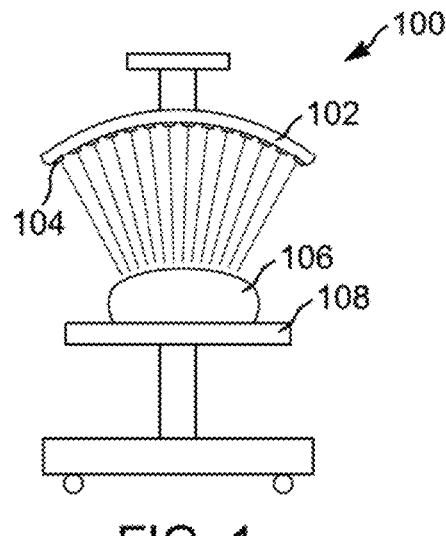
FIG. 1 shows a side view of an embodiment of an operating room lighting system according to the invention.

As required, embodiments are disclosed herein; however, it is to be understood that the disclosed embodiments are merely examples and that the devices and methods described below can be embodied in various forms. Therefore, specific structural and functional details disclosed herein are not to be interpreted as limiting, but merely as a representative basis for teaching one skilled in the art to variously employ the present subject matter in virtually any appropriately detailed structure and function. Further, the terms and phrases used herein are not intended to be limiting, but rather, to provide an understandable description of the concepts.

It can be advantageous to set forth definitions of certain words and phrases used throughout this disclosure. The terms "a" or "an", as used herein, are employed to describe elements and components described herein. This is done merely for convenience and to give a general sense of the scope of the disclosure. This description should be read to include one or at least one and the singular also includes the plural unless it is obvious that it is meant otherwise. The term plurality, as used herein, is defined as two or more than two. The term another, as used herein, is defined as at least a second or more. The term "coupled," as used herein, is defined as "connected," although not necessarily directly, and not necessarily mechanically.

The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A; B; C; A and B; A and C; B and C; and A, B, and C.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

Note that not all of the activities described in the general description or the examples are required, that a portion of a specific activity may not be required, and that one or more further activities can be performed in addition to those described. Still further, the order in which activities are listed are not necessarily the order in which they are performed.

In general, the invention relates to an automated lighting system for operating rooms that aims and focuses light into a work area while eliminating shadows. Mounted to a boom system, akin to traditional operating room lights, adjustments to the lighting can be made conveniently, with little or no manual adjustment of the lights. The disclosed automated lighting system allows a surgeon to easily define a target region with some type of user interface, then lights automatically adjust based on the surgeon defined target region to illuminate the target region.

Figure 2:
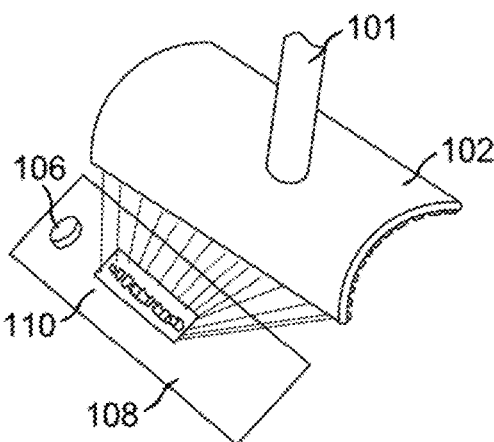
FIG. 2 shows a top view of the system of FIG. 1.

FIGS. 1 and 2 show one embodiment of system 100 comprising a curved panel 102 of an array of individually controllable LEDs 104. Curved panel 102 is located above patient 106 lying on operating table 108 and is connected or otherwise coupled to boom 101. In an exemplary embodiment array of LEDs 104 incorporates both diffuse lights and spotlights to counter shadows while still having a large illuminance value of a zone of illumination 110 (FIG. 2), which in this case is the area of wound or surgical site.

Figure 3:
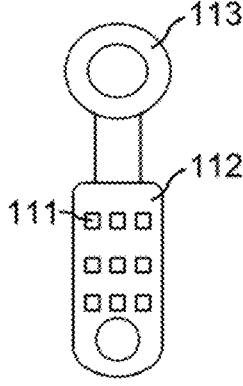
FIG. 3 shows a first embodiment of a wand for controlling an operating room lighting system.

FIG. 3 shows a wand 112 that functions to define zone of illumination 110. In an exemplary embodiment, wand 112 incorporates a tracker 113 that interfaces with a tracking system such as those used in surgical navigation or robotic surgical systems to define zone of illumination 110 by pointing or placing wand 112 at the periphery of zone of illumination 110.

After zone of illumination 110 is identified, a wired or wireless connection (such as Bluetooth or WiFi) between wand 112 and curved panel 102 controls array of LEDs 104 to illuminate the surgical site on patient 106. Controls 111 on wand 112 can be used to adjust both the size, location, and illumination intensity of zone of illumination 110.

Figure 4:
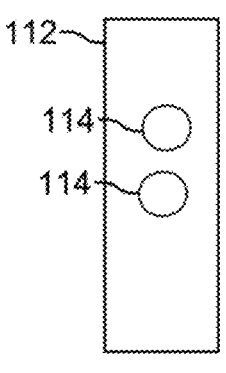
FIG. 4 shows a second embodiment of a wand for controlling an operating room lighting system.
Figure 5:
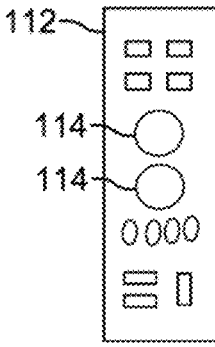
FIG. 5 shows a third embodiment of a wand for controlling an operating room lighting system.

FIGS. 4 and 5 show other embodiments of wand 112, with the wand of FIG. 5 having functionality so that more interactions with the lighting system can be achieved than with the wand of FIG. 4. With the wand of FIG. 4, controls 114 are used to define edges of zone of illumination 110 with other interactions with the lighting system achieved through another interface such as a computer or panel of controls located elsewhere. With the wand of FIG. 5, controls 114 are used to define edges of the zone of illumination 110 as well as other interactions with the lighting system.

Figure 6:
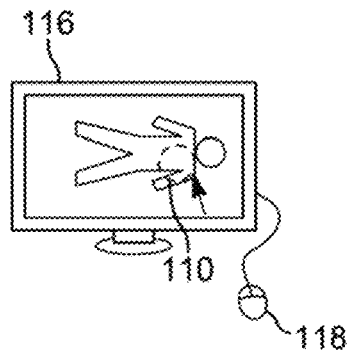
FIG. 6 shows a computer mouse as an example of other representative devices that can be used either in conjunction with the wand or without the wand such as an Ipad or similar touch screen device to define the zone of illumination.
Figure 7:
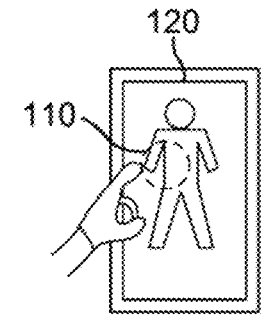
FIG. 7 shows a touchscreen as an example of other representative devices that can be used either in conjunction with the wand or without the wand to define the zone of illumination.
Figure 8:
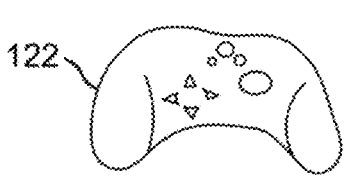
FIG. 8 shows a game console controller style input device as an example of other representative devices that can be used either in conjunction with the wand or without the wand such as an Ipad or similar touch screen device to define the zone of illumination.
Figure 9:
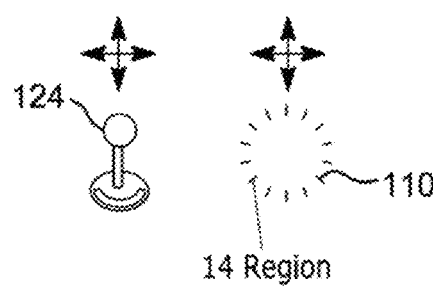
FIG. 9 shows a joystick as an example of other representative devices that can be used either in conjunction with the wand or without the wand such as an Ipad or similar touch screen device to define the zone of illumination.

FIGS. 6-9 show examples of other representative devices that can be used either in conjunction with wand 112 or without wand 112 to define zone of illumination 110. In FIG. 6, a computer 116 displays live video feed of the surgical site. Using a mouse 118 or similar device, zone of illumination 110 is drawn and defined on the computer screen. Similarly, FIG. 7 shows a touchscreen 120 displaying a live video feed of the surgical site so that zone of illumination 110 is drawn and defined on touchscreen 120. In FIG. 8, a computer again displays a live video feed of the surgical site and zone of illumination 110 is drawn with a controller 122 with functionality like a gaming controller. FIG. 9 shows a variation that does not need a live video feed. Specifically, a default region of light (which can vary based on the surgical procedure to be performed) is adjusted using joystick 124 to zoom in or out and move the light left and right and up and down.

As is evident for FIGS. 3-9 and the above description, the user interface can be such that all functionality is on the wand, with all interactions (zone of illumination definition, brightness adjustment, etc.) with the lighting system through the wand. Alternatively or in addition, a computer and/or touchscreen can be used for some or all functionality (ranging from zone of illumination definition to auxiliary capabilities such as controlling cameras). Alternatively or in addition, some portion of the functionality can be on a separate controller with a panel of buttons. The invention contemplates combinations of these user interfaces.

In order to conform to typical operating room safety, standards and procedures, the lighting system 100 (as well as to be described lighting system 200) preferably uses lights with a brightness between 40,000 and 160,000 Lux as measured from 1.64 feet from the source; the color temperature of white light is between 3000 and 6700 K; the noise emitted by the system does not exceed 95 dB; the system interfaces with standard wall outlets in the operating room (120 VAC or 220 VAC); the power consumption is less than 200 W overall; and components of the system that the surgeon interacts with are sterilizable.

Ideally, the lighting system 100, 200 is capable of lighting any region in a 2 ft×2 ft workspace, which is the size for many surgical procedures. The lighting system can provide one or two zones of illumination having a substantially rectangular or elliptical shape between 4 inches and 2.5 ft in diameter. The brightness in the zone of illumination is adjustable and appears uniform as detected by the human eye.

Figure 10:
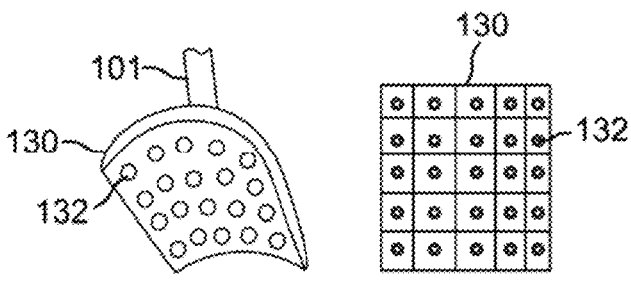
FIG. 10 show an embodiment of an arrangement of lights that can be used for the operating room lighting system according to the invention.
Figure 11:
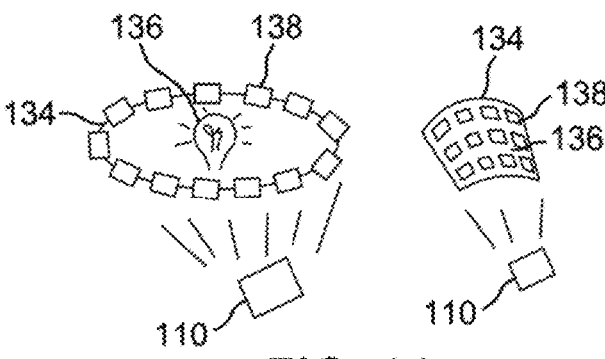
FIG. 11 show another embodiment of an arrangement of lights that can be used for the operating room lighting system according to the invention.
Figure 12:
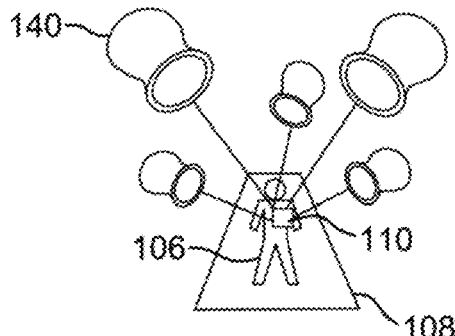
FIG. 12 show another embodiment of an arrangement of lights that can be used for the operating room lighting system according to the invention.
Figure 13:
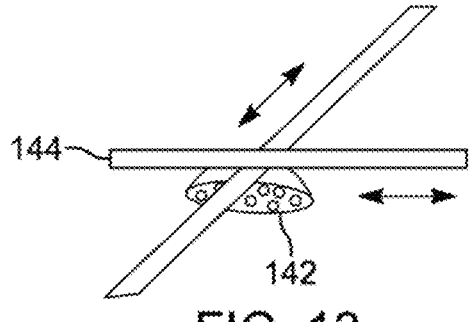
FIG. 13 show another embodiment of an arrangement of lights that can be used for the operating room lighting system according to the invention.

With the above taken into consideration, FIGS. 10-13 show different arrangements of lights that can be used for the operating room lighting system according to the invention. These arrangements can be used separately or in combination. FIG. 10 shows a dynamic light array 130 with a plurality of directed LEDs 132, each with two axes of rotation. Each LED 132 can be moved separately, like the eyes of a chameleon. FIG. 11 shows a dynamic mirror array 134 which includes at least one light source 136 and array of mirrors 138. At least some of mirrors 134 can independently rotate about one or two axes of rotation. FIG. 12 shows an arrangement of LED spotlights 140. At least some of spotlights 140 are on individually controllable booms with zoom control to adjust the size of zone of illumination 110. FIG. 13 shows a small cluster 142 of directed LEDs at various angles. Cluster 142 is on a two-axis rail system 144 to change the location. Zoom control is used to adjust the zone of illumination size.

Figure 14:
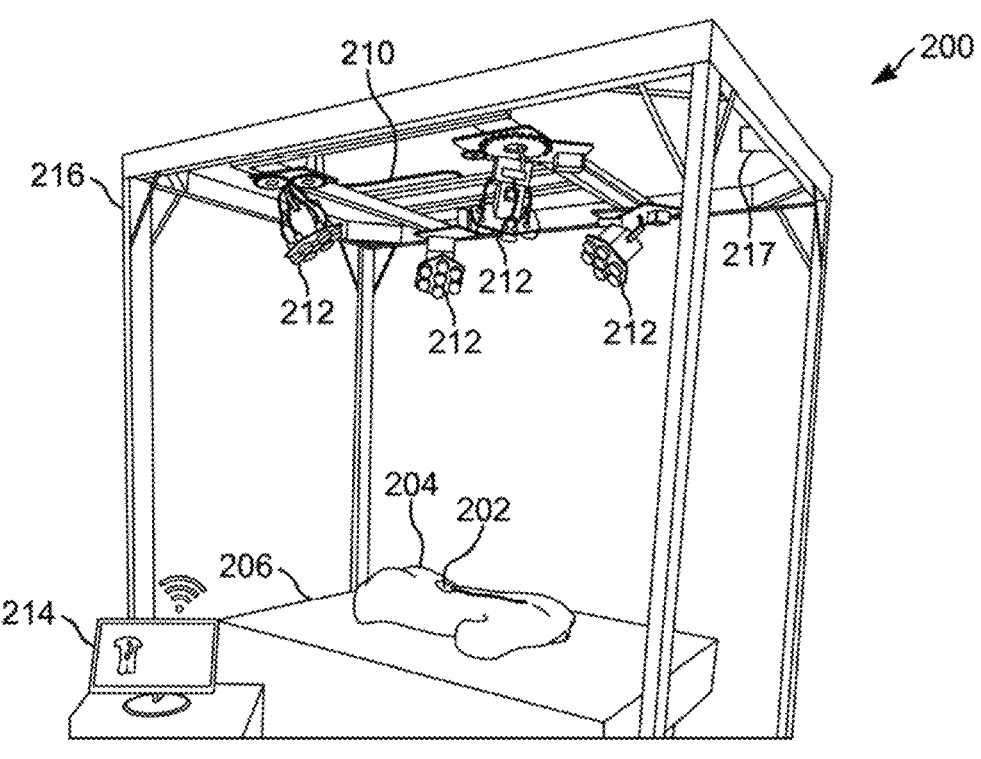
FIG. 14 shows an exemplary embodiment of an operating room lighting system according to the invention.
Figure 15:
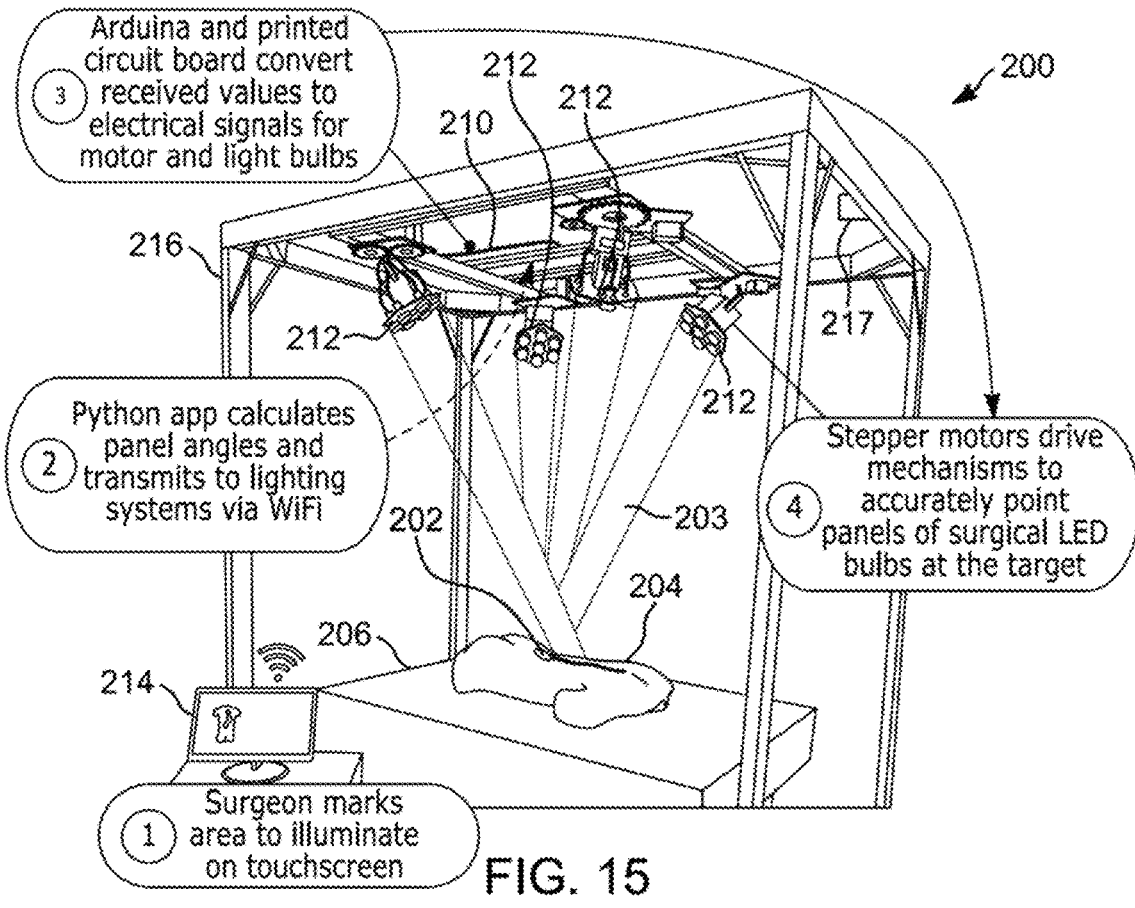
FIG. 15 shows the operating room lighting system of FIG. 14 in use to light a zone of illumination.

FIGS. 14-22 and the following description relate to an exemplary embodiment of an operating room system 200 for illuminating a target region such as surgical site 202 (or any other location of interest) of a patient 204 on an operating table 206. FIGS. 14 and 15 show that system 200 comprises a mounting structure 210, a plurality of light panels 212, and a user interface 214. Mounting structure 210 couples the plurality of light panels 212 and holds the electronics and mechanics (both of which are detailed below) for controlling the plurality of light panels 212 to illuminate surgical site 202 to create a zone of illumination (ZOIL) 203 as desired by a user operating user interface 214. Although the plurality of light panels 212 is shown as four panels, the present invention contemplates the use of any suitable number of light panels 212.

Although mounting structure 210 is shown held to a frame 216 which is made to fit around operating table 206 and hold mounting structure 210 approximately eight feet in the air or any suitable distance, mounting structure could be held by a boom, which are typically already present in an operating room. Frame 216 can be provided with lockable wheels for ease of maneuverability until properly positioned at which point the wheels can be locked.

In addition to mounting structure 210, an imager such as camera 217 is mounted onto frame 216. A video feed from camera 217 of operating table 206 is shown so that user interface 214 can be used to define the exact area of the surgical cavity to bring into focus. Alternatively (i.e. camera 217 is optional) or additionally video feed(s) from cameras already present in the operating room can be used with user interface 214 to define the exact area of the surgical cavity to bring into focus. As one of ordinary skill in the art is aware and would understand how to accomplish from surgical navigation or related technologies, video feed from camera 217 should be calibrated so that the images from camera 217 are translated into coordinates in the "real world".

Figure 16:
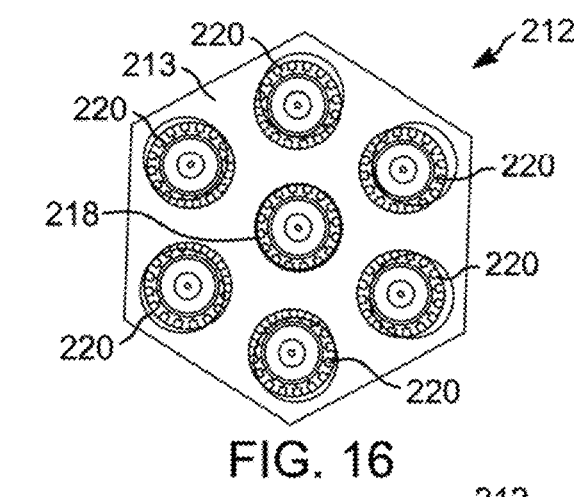
FIG. 16 is a bottom view of one of the light panels of the operating room lighting system of FIG. 14.
Figure 17:
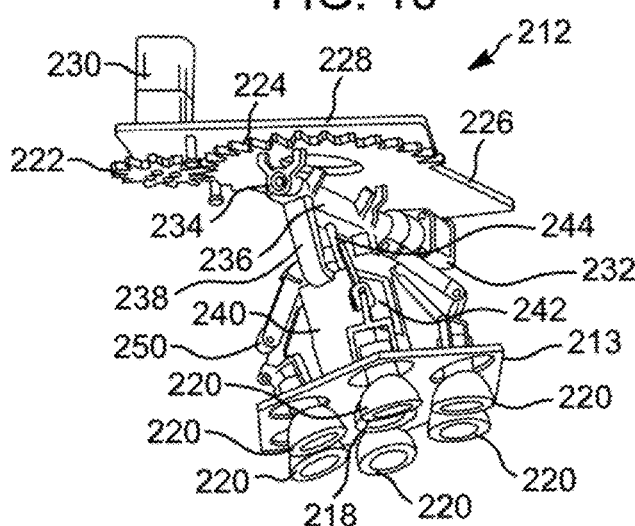
FIG. 17 is a perspective view of the light panel of FIG. 16.
Figure 18:
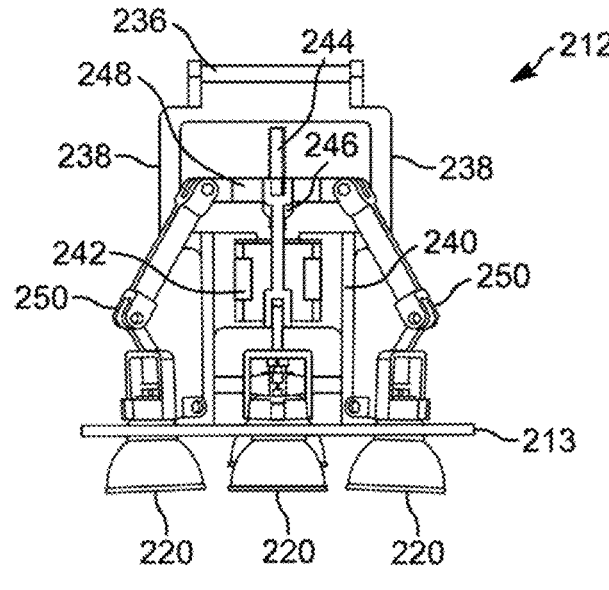
FIG. 18 is a side view of the light panel of FIG. 16.

Turning now to FIGS. 16-18, the plurality of light panels 212 is now described. In FIGS. 16-18, the electrical connections are not shown to facilitate understanding of the mechanical mechanisms. Each light panel 212 includes an array of lights that extend through holes in platform 213. In the shown embodiment, a central light 218 is surrounded by peripheral lights 220. As shown, six peripheral lights 220 form a hexagonal pattern around central light 218. The present invention contemplates the use of any suitable array of lights, both with and without central light 218.

If central light 218 is used, central light 218 can be the same type of light as peripheral lights 220 or a different type of light than peripheral lights 220. For example, peripheral lights 220 can be narrow-angle spotlights, with central light 218 also being a narrow-angle spotlight or a diffuse spotlight. A non-limiting example of a narrow-angle spotlight is a dimmable narrow beam angle LED (MR16, 8 W, approximately 400 lumens, 3000K temperature) and a non-limiting example of a diffuse spotlight is a dimmable LED (PAR 30, 14 W, approximately 1200 lumens, 3000K temperature).

As should be evident, the plurality of light panels 212 serve as overhead lightbulb clusters to direct light at the target region. The mechanical mechanisms for directing light at the target region are now described. Light panel 212 has two axes of rotation (yaw and pitch) so it can aim lights 218, 220 at the target region. The yaw and pitch movements allow light panels 212 to adjust to be angled toward the desired region as set and determined by user interface 214. A yaw gear 222 engages a gear cutout 224 of a bearing plate 226 for rotational movement in a plane parallel to a base 228. Yaw gear 222 rotates when actuated by an actuator, which in this case is a yaw stepper motor 230.

For pitch control (i.e. rotation or tilting in a plane orthogonal to base 228), actuation of an actuator, which in this is a pitch stepper motor 232, rotates a shaft 234 causing base member 236 to also rotate. One or more arms 238 extend from base member 236 to a pedestal 240, which is mounted to platform 213.

In addition to yaw and pitch adjustment, a focus mechanism adjusts the aim of peripheral lights 220 to make the area light on table 206 selectively bigger and smaller. The focus mechanism uses an actuator, which in this case is a focus stepper motor 242 with a lead screw 244 and a nut 246 to translate rotational motion of motor 242 into linear motion. Nut 246 is held in place with a plate 248, which has mechanical linkages 250 with joints to sweep peripheral lights 220 back and forth, i.e. toward and away from central light 218. In other words, each linkage 250 can be contracted or expanded, allowing for peripheral lights 220 to angle in and out for focus by making the area light on table 206 selectively bigger and smaller.

In summary, system 200 uses four three-axis mechanisms (one for each light panel 212) to direct the light and effectively eliminate shadows. The yaw and pitch axis serve to aim the spotlight anywhere on the 2D plane (operating table 206). The focus mechanism is designed to adjust the aim of the individual lights to make the spotlight on table 206 bigger and smaller.

Figure 19:
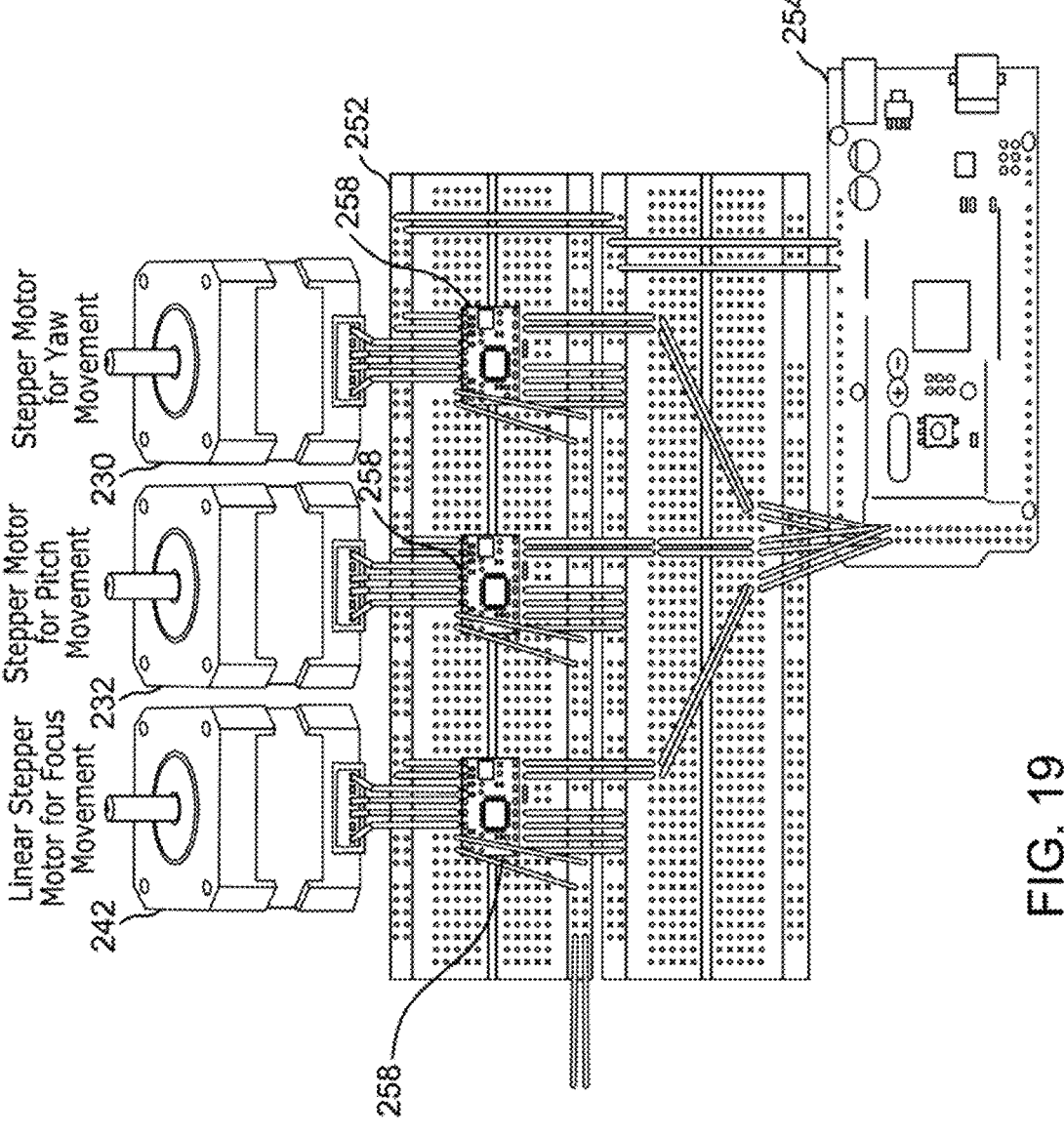
FIG. 19 shows an embodiment of control hardware used to control each of the light panels of the operating room lighting system of FIG. 14.

With reference to FIG. 19, the electronics for actuation of yaw motor 230, pitch motor 232, and focus motor 242 for each of the plurality of light panels 212 are schematically shown. Motor control hardware 252 is connected to a microcontroller board 254 (a non-limited example is Arduino Mega 2560). Each of the plurality of light panels 212 would have separately controllable motor control hardware 252. Microcontroller board 254 receives input from a processor 256 (shown in FIG. 22). The input is based on information received from user interface 214. Processor 256 calculates target angles and positions for motors 230, 232, 242 and microcontroller board 254 converts the target angles and positions to actual movements through drivers 256, which are used to drive motors 230, 232, 242.

Figure 20:
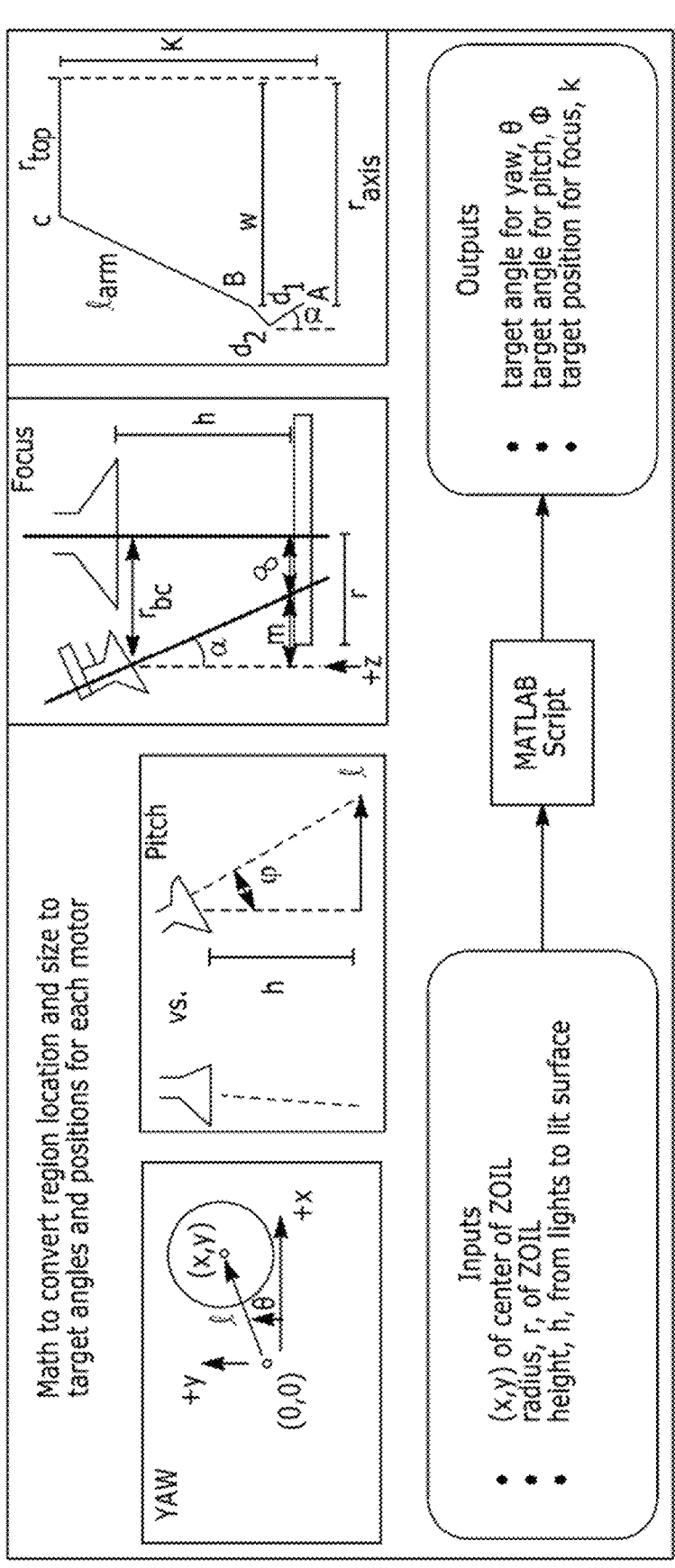
FIG. 20 shows exemplary calculations to convert target region location and size to target angles and position used by the control hardware of FIG. 19 for each motor.

FIG. 20 shows exemplary calculations to convert ZOIL 203 location and size to target angles and position for motors 230, 232, 242. In general, microcontroller board 254 receives an input from processor 256 of a target pitch and yaw angle, as well as a target height of the linear actuator for the focus mechanism. Once received by microcontroller board 254, the target position is converted into a target number of motor steps from the reference position using the relevant gear ratios and steps per revolution. These are then converted into electronic STEP and DIR signals, which drive motors 230, 232, 242 to the target position. Although FIG. 20 shows MATLAB used for the calculations, and suitable software of app could be used.

Figure 21:
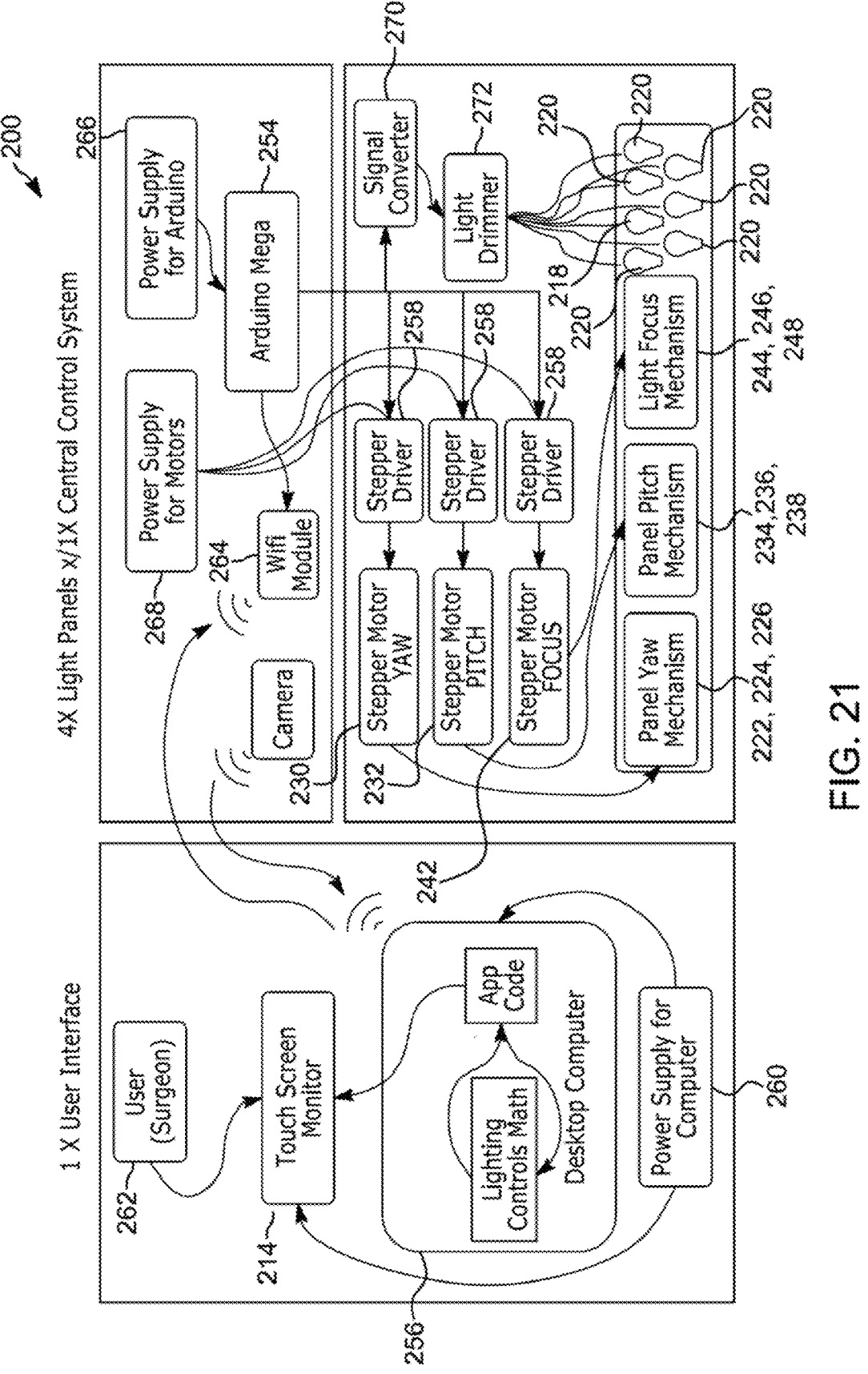
FIG. 21 is a schematic diagram showing use of an embodiment of the operating lighting system of FIG. 14.

FIG. 21 schematically shows the components of system 200 and how they are used. Recorded or live view from camera 217 of patient 204 on table 206 is wirelessly transmitted to processor 256 (in this case a desktop computer with a power supply 260) and displayed on user interface 214 (in this case a touchscreen monitor), user 262 (such as a surgeon) can select and drag a region on touchscreen 214 to define zone of illumination 203. Processor 256 performs the calculations outlined in FIG. 20 and associated text as well as any other image processing. This data from processor 256 is wirelessly transmitted via Wifi module 264 to microcontroller board 254, which is powered by a power supply 266. The present invention contemplates that any other suitable means for wirelessly transmitting data could be used.

Based on the transmitted data, microcontroller board 254 provides instructions to drivers 258 to activate motors 230, 232, 242, which receive power from a motor power supply 268. Via the mechanisms discussed above, motors 230, 232, 242 adjust yaw, pitch, and focus of light panel 212 to light ZOIL 203. As discussed above, lights 218, 220 can be dimmable, in which case microcontroller board 254 can also control the brightness of lights 218, 220. For example, using ambient room lighting, a desired brightness can be determined and microcontroller board 254 will use signal converter 270 to adjust the brightness of lights 218, 220 with a light dimmer 272.

Although FIG. 21 shows only one light panel 212 of the plurality of light panels, user interface and central control system would control, either individually or collectively, the rest of the light panels as well.

Figure 22:
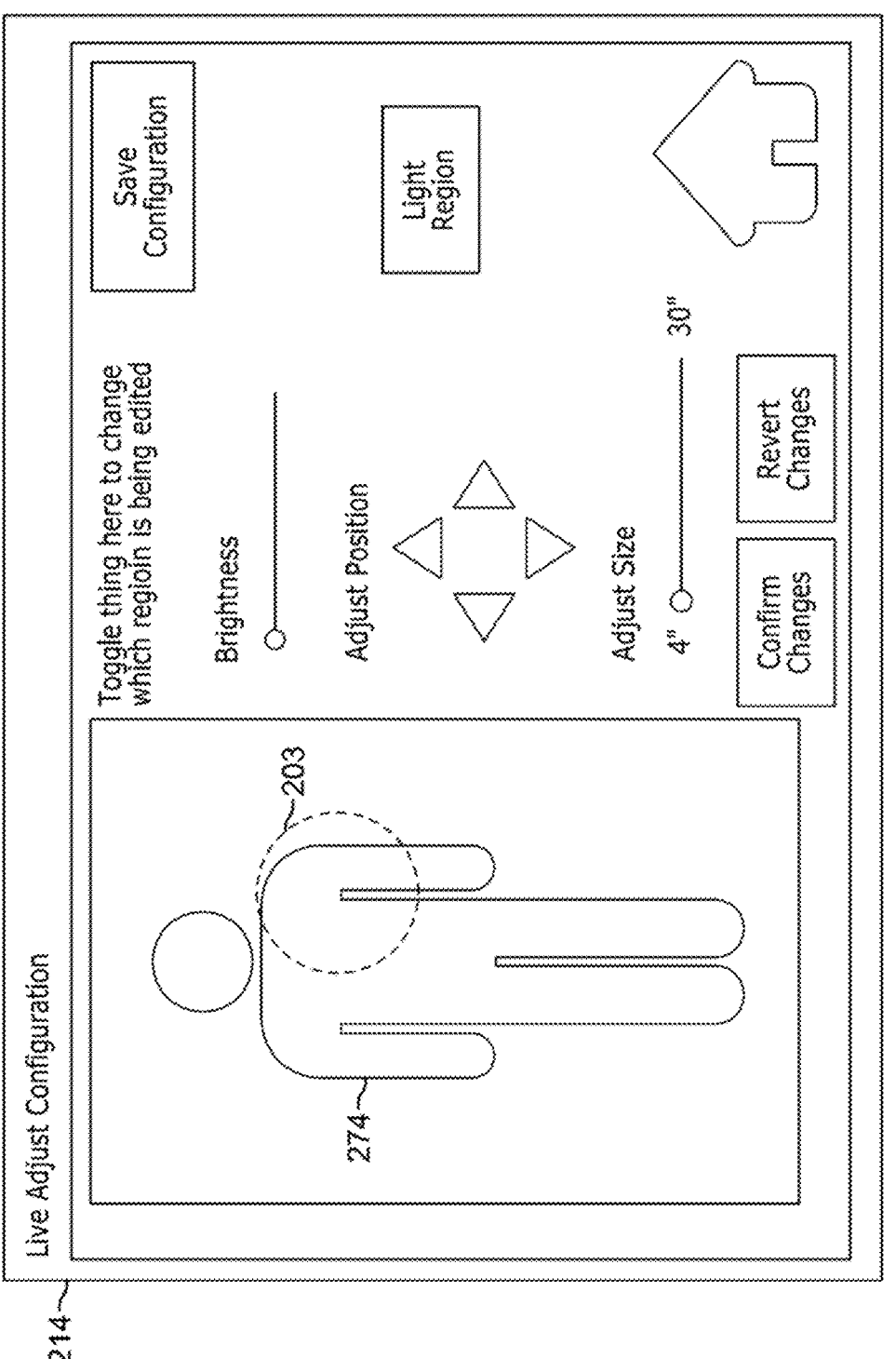
FIG. 22 shows an embodiment in which a touchscreen is used to define the zone of illumination.

After initially defining ZOIL 203, user 262 can use touchscreen 214 to change ZOIL 203 location, size, and/or brightness as illustrated in FIG. 22. In this regard, XOIL 203 is superimposed on image (either live stream or record) 274 of the patient. As the invention envisions multiple cameras can be used, the camera(s) in use can be selected by touchscreen 214. A photo can be taken to define the field for lights and select the camera to record. Multiple cameras can be utilized to give different perspectives of the same portion of the field.

All references cited herein are expressly incorporated by reference in their entirety. It will be appreciated by persons skilled in the art that the invention is not limited to what has been particularly shown and described herein above. In addition, unless mention was made above to the contrary, it should be noted that all the accompanying drawings are not to scale. There are many different features to the invention, and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the invention set forth herein that are within the scope and spirit of the present invention are to be included as further embodiments of the invention.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112 (f) unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the disclosure, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any sub-combination. Further, references to values stated in ranges include each and every value within that range.

The above discussion is meant to be illustrative of the principles and various embodiments of the present invention. Numerous variations and modifications will become apparent to those skilled in the art once the above disclosure is fully appreciated.

What is claimed is:

1. An operating room lighting system for illuminating a target region of a patient, the system comprising:
a plurality of light panels for providing light;

a user interface that includes a screen displaying a live stream or recorded video camera image of the patient and an input device usable by a user to select a zone of illumination;

a processor for using the live stream or recorded video camera image of the patient and the user selected zone of illumination to calculate yaw, pitch, and focus adjustments of the plurality of light panels to illuminate the target region; and actuator means for using the calculated yaw, pitch, and focus adjustments to move the plurality of light panels so that the provided light from the plurality of light panels illuminates the target region, wherein each of the plurality of light panels includes a plurality of peripheral lights surrounding a central light;

wherein the actuator means comprises a separate yaw adjustment assembly, pitch adjustment assembly, and focus adjustment assembly for each of the plurality of light panels; and wherein the yaw adjustment assembly and the pitch adjustment assembly adjust the plurality of light panels to be angled toward the target region as set and determined by the user interface and the focus adjustment assembly adjusts aim of the peripheral lights to make an area light on the target region selectively bigger and smaller as set and determined by the user interface.

2. The system of claim 1, wherein the user interface is a touchscreen monitor that includes the screen displaying the live stream or recorded video camera image of the patient and the input device usable by a user to select a zone of illumination to illuminate the target region.

3. The system of claim 1, wherein the plurality of light panels and the processor are mounted on a mounting structure.

4. The system of claim 3, wherein the mounting structure is mounted to a frame which is made to fit around an operating table holding the patient and to hold the mounting structure at a height so that the plurality of light panels provides light to at least the target region.

5. The system of claim 4, wherein a video camera is attached to the frame, the video camera providing the live stream or recorded video camera image of the patient.

6. The system of claim 3, wherein the mounting structure is mountable to an operating room boom.

7. The system of claim 1, wherein each of the plurality of peripheral lights includes six peripheral lights arranged in a hexagonal pattern around the respective central light.

8. The system of claim 7, wherein the central light is a diffuse spotlight or a narrow-angle spotlight and each of the peripheral lights is a narrow-angle spotlight.

9. The system of claim 1, wherein the separate yaw adjustment assembly for each of the plurality of light panels comprises:
a base;
a bearing plate from which the plurality of peripheral lights surrounding the central light extend, the bearing plate rotatably mounted on the base for rotational movement of the bearing plate relative to the base in a plane parallel to a plane of the base, wherein the bearing plate includes a gear cutout;
a yaw gear engageable with the gear cutout; and
a yaw motor for rotating the yaw gear when actuated.

10. The system of claim 9, wherein the separate pitch adjustment assembly for each of the plurality of light panels comprises:
a pitch motor;

11 a shaft coupled to the pitch motor to rotate when the pitch motor is actuated;

a base member mounted to the bearing plate via brackets and operatively associated with the shaft to rotate when the shaft rotates, wherein one or more arms extend from base member to a pedestal mounted on a platform which holds electrical sockets for the plurality of peripheral lights and the central light.

11. The system of claim 10, wherein the separate focus adjustment assembly for each of the plurality of light panels comprises:

a focus motor with a lead screw and nut to translate rotational motion into linear motion;

a plate holding nut in place; and mechanical linkages extending from the plate to the electrical socket of each of the plurality of peripheral lights, wherein the mechanical linkages include at least one joint and the electrical sockets of the plurality of peripheral lights are pivotably connected to the pivot, and wherein actuation of the focus motor in a first direction causes the plurality of peripheral lights to angle toward the central light and actuation of the focus motor in a second direction causes the plurality of peripheral lights to angle away from the central light.

12. The system of claim 11, wherein actuation of the yaw motor, pitch motor, and focus motor is controlled by motor control hardware, the motor control hardware comprising:

a microcontroller that receives the calculated yaw, pitch, and focus adjustments and converts the adjustments to yaw, pitch, and focus driver data;

a yaw motor driver for receiving the yaw driver data to actuate the yaw motor;

a pitch motor driver for receiving the pitch driver data to actuate the pitch motor; and a focus motor driver for receiving the focus driver data to actuate the focus motor.

13. The system of claim 12, wherein the processor receives user input from the input device to change at least one of the calculated yaw, pitch, and focus adjustments of the plurality of light panels to illuminate the target region.

14. The system of claim 1, wherein each of the plurality of light panels include at least one light that is dimmable.

15. An operating room lighting system for illuminating a target region of a patient, the system comprising:

a plurality of light panels for providing light, each of the plurality of light panels comprising a plurality of peripheral lights surrounding a central light;

a user interface that includes a screen displaying a live stream or recorded video camera image of the patient and an input device usable by a user to select a zone of illumination;

a processor for using the live stream or recorded video camera image of the patient and the user selected zone of illumination to calculate yaw, pitch, and focus adjustments of the plurality of light panels to illuminate the target region; and actuator means for using the calculated yaw, pitch, and focus adjustments to move the plurality of light panels so that the provided light from the plurality of light panels illuminates the target region,

wherein the actuator means comprises a separate yaw adjustment assembly, pitch adjustment assembly, and focus adjustment assembly for each of the plurality of light panels;

wherein the separate yaw adjustment assembly for each of the plurality of light panels comprises:

a base;

a bearing plate from which the plurality of peripheral lights surrounding the central light extend, the bearing plate rotatably mounted on the base for rotational movement of the bearing plate relative to the base in a plane parallel to a plane of the base, wherein the bearing plate includes a gear cutout;

a yaw gear engageable with the gear cutout; and a yaw motor for rotating the yaw gear when actuated;

wherein the separate pitch adjustment assembly for each of the plurality of light panels comprises:

a pitch motor;

a shaft coupled to the pitch motor to rotate when the pitch motor is actuated;

a base member mounted to the bearing plate via brackets and operatively associated with the shaft to rotate when the shaft rotates, wherein one or more arms extend from base member to a pedestal mounted on a platform which holds electrical sockets for the plurality of peripheral lights and the central light wherein the separate focus adjustment assembly for each of the plurality of light panels comprises:

a focus motor with a lead screw and nut to translate rotational motion into linear motion;

a plate holding nut in place; and mechanical linkages extending from the plate to the electrical socket of each of the plurality of peripheral lights, wherein the mechanical linkages include at least one joint and the electrical sockets of the plurality of peripheral lights are pivotably connected to the pivot, and wherein actuation of the focus motor in a first direction causes the plurality of peripheral lights to angle toward the central light and actuation of the focus motor in a second direction causes the plurality of peripheral lights to angle away from the central light.

16. The system of claim 15, wherein actuation of the yaw motor, pitch motor, and focus motor is controlled by motor control hardware, the motor control hardware comprising:

a microcontroller that receives the calculated yaw, pitch, and focus adjustments and converts the adjustments to yaw, pitch, and focus driver data;

a yaw motor driver for receiving the yaw driver data to actuate the yaw motor;

a pitch motor driver for receiving the pitch driver data to actuate the pitch motor; and a focus motor driver for receiving the focus driver data to actuate the focus motor.

17. The system of claim 16, wherein the processor receives user input from the input device to change at least one of the calculated yaw, pitch, and focus adjustments of the plurality of light panels to illuminate the target region.

* * * * *